(12) United States Patent
Gloth

(10) Patent No.: US 8,147,399 B2
(45) Date of Patent: Apr. 3, 2012

(54) DEVICE AND METHOD FOR APPLYING A BIOCOMPATIBLE SUBSTANCE TO A FEMALE STIMULATION DEVICE

(76) Inventor: David A. Gloth, Boston, MA (US)

( * ) Notice: Subject to any disclaimer, the term of this patent is extended or adjusted under 35 U.S.C. 154(b) by 1585 days.

(21) Appl. No.: 11/401,618

(22) Filed: Apr. 10, 2006

(65) Prior Publication Data

US 2006/0206000 A1      Sep. 14, 2006

Related U.S. Application Data

(63) Continuation-in-part of application No. 11/008,332, filed on Dec. 9, 2004, now Pat. No. 7,670,280, which is a continuation-in-part of application No. 10/842,957, filed on May 11, 2004, now Pat. No. 6,949,067.

(51) Int. Cl.
*A61F 5/00* (2006.01)
(52) U.S. Cl. .......................................................... 600/38
(58) Field of Classification Search ................. 15/210.1; 600/38–41; 607/6, 12, 78–81, 114, 1, 96, 607/108; 128/897, 898; 604/1, 304, 305
See application file for complete search history.

(56) References Cited

U.S. PATENT DOCUMENTS

| | | | | |
|---|---|---|---|---|
| 713,761 | A | * | 11/1902 | Harlan .............................. 601/6 |
| 2,000,710 | A | * | 5/1935 | Miller .............................. 601/6 |
| 2,120,367 | A | | 6/1938 | Lewis |
| 2,212,706 | A | | 8/1940 | Cohn et al. |
| 2,258,547 | A | * | 10/1941 | Dodds ......................... 15/210.1 |
| 2,711,172 | A | | 6/1955 | Booth |
| 2,792,003 | A | * | 5/1957 | Cantor |
| 3,463,302 | A | * | 8/1969 | Preston .......................... 206/361 |
| 4,224,933 | A | | 9/1980 | Reiling |
| 4,312,348 | A | * | 1/1982 | Friese ............................. 604/363 |
| 4,740,194 | A | * | 4/1988 | Barabino et al. .................. 604/3 |
| D320,084 | S | | 9/1991 | Stewart |
| 5,067,480 | A | | 11/1991 | Woog et al. |
| 5,103,810 | A | | 4/1992 | Chang |
| 5,333,621 | A | | 8/1994 | Denzer |
| 5,690,603 | A | | 11/1997 | Kain |
| 5,725,473 | A | | 3/1998 | Taylor |
| 5,755,236 | A | | 5/1998 | Dann et al. |
| 5,813,973 | A | | 9/1998 | Gloth |
| 5,853,362 | A | | 12/1998 | Jacobs |
| 5,877,216 | A | | 3/1999 | Place et al. |

(Continued)

FOREIGN PATENT DOCUMENTS

EP        289587 A1    11/1988

(Continued)

OTHER PUBLICATIONS

"FDA Clears New Sexual Therapy Device," Medical Letter on the CDC & FDA, May 20, 2000, Charles W. Henderson, Atlanta, GA.

(Continued)

*Primary Examiner* — Samuel Gilbert

(57) ABSTRACT

In one aspect, the invention provides a female stimulation system that includes a device body having an operating region and a body contacting surface, and means for controlling a vacuum produced by the device body when the device body is applied to a user. In addition, the female stimulation system includes an applicator adapted to apply a biocompatible substance to the body contacting surface. In one or more embodiments, the applicator may be a pad, form-fitted insert, or a capsule.

56 Claims, 7 Drawing Sheets

U.S. PATENT DOCUMENTS

| | | | |
|---|---|---|---|
| 5,885,233 | A | 3/1999 | Adachi |
| 5,895,349 | A * | 4/1999 | Tihon .............................. 600/29 |
| 5,920,923 | A | 7/1999 | Jillette |
| 5,928,134 | A * | 7/1999 | Vergara ........................... 600/38 |
| 5,989,180 | A | 11/1999 | Norton et al. |
| 5,997,469 | A | 12/1999 | Northcutt |
| 6,056,705 | A | 5/2000 | Stigar-Brown |
| 6,067,663 | A | 5/2000 | Fernandez |
| 6,099,463 | A | 8/2000 | Hockhalter |
| 6,132,366 | A | 10/2000 | Ritchie et al. |
| 6,179,774 | B1 | 1/2001 | Landry |
| 6,179,775 | B1 | 1/2001 | Thompson |
| D443,057 | S | 5/2001 | Hovland et al. |
| 6,224,541 | B1 | 5/2001 | Thompson |
| 6,246,915 | B1 | 6/2001 | Boutos |
| 6,250,304 | B1 | 6/2001 | Turner |
| 6,294,550 | B1 | 9/2001 | Place et al. |
| D449,690 | S | 10/2001 | Hovland et al. |
| 6,306,841 | B1 | 10/2001 | Place et al. |
| 6,322,493 | B1 | 11/2001 | Thompson |
| 6,464,653 | B1 | 10/2002 | Hovland et al. |
| 6,469,016 | B1 | 10/2002 | Place et al. |
| 6,537,260 | B1 | 3/2003 | Lamb |
| 6,578,205 | B1 | 6/2003 | King |
| 6,593,313 | B2 | 7/2003 | Place et al. |
| 6,702,733 | B1 | 3/2004 | Thompson |
| 6,733,438 | B1 * | 5/2004 | Dann et al. ....................... 600/38 |
| 6,749,557 | B2 | 6/2004 | Garland |
| D494,676 | S | 8/2004 | Dubniczki et al. |
| 6,923,755 | B2 | 8/2005 | Norma |
| 6,935,343 | B1 | 8/2005 | Turner |
| 2001/0051656 | A1 | 12/2001 | Place et al. |
| 2002/0013289 | A1 | 1/2002 | Pendergast et al. |
| 2002/0165429 | A1 | 11/2002 | Thompson |
| 2002/0177582 | A1 | 11/2002 | Maloney |
| 2003/0023139 | A1 | 1/2003 | Hartz |
| 2003/0170325 | A1 | 9/2003 | Mermelstein et al. |
| 2003/0171647 | A1 | 9/2003 | Garland |
| 2003/0207852 | A1 | 11/2003 | Place et al. |
| 2004/0044328 | A1 | 3/2004 | Kemp et al. |
| 2004/0059190 | A1 | 3/2004 | Matlock |
| 2004/0186344 | A1 | 9/2004 | Jannuzzi |
| 2004/0230093 | A1 | 11/2004 | Marshall |
| 2004/0260252 | A1 | 12/2004 | Dipiano et al. |
| 2005/0124853 | A1 | 6/2005 | Norma |
| 2005/0165367 | A1 | 7/2005 | Higgins |
| 2006/0047182 | A1 | 3/2006 | Cochran |

FOREIGN PATENT DOCUMENTS

| | | |
|---|---|---|
| EP | 861067 | 9/1998 |
| JP | 3212793 | 7/2003 |
| WO | WO 97/28766 A1 | 8/1997 |
| WO | WO 99/21562 | 5/1999 |
| WO | WO 00/28939 A2 | 5/2000 |
| WO | WO 2004/058134 A2 | 7/2004 |
| WO | WO 2004/064913 A1 | 8/2004 |
| WO | WO 2005/072319 A2 | 8/2005 |

OTHER PUBLICATIONS

Laviolette and Meuner, "Vaginal Dryness," Quebec Pharmacie (Canada), Nov.-Dec. 2004, vol. 51 (Abstract).

PCT International Search Report for International Application No. PCT/US2005/016539 mailed Aug. 24, 2005.

\* cited by examiner

DEVICE AND METHOD FOR APPLYING A BIOCOMPATIBLE SUBSTANCE TO A FEMALE STIMULATION DEVICE

RELATED APPLICATIONS

This application is a continuation-in-part under 35 U.S.C. §120 of co-pending U.S. patent application Ser. No. 11/008,332, filed Dec. 9, 2004, which is a continuation-in-part under 35 U.S.C. §120 of U.S. patent application Ser. No. 10/842,957, filed May 11, 2004, and issued on Sep. 27, 2005 as U.S. Pat. No. 6,949,067 which are each herein incorporated by reference in their entirety.

BACKGROUND OF INVENTION

1. Field of Invention

Embodiments of the invention relate generally to female sexual stimulation systems and devices and, more specifically, to a device and method to apply a biocompatible substance to a female sexual stimulation device.

2. Discussion of Related Art

Clitoral vascular engorgement plays an important role in female sexual arousal and satisfaction. The most effective method of increasing clitoral engorgement, especially in women suffering from Female Sexual Dysfunction ("FSD") is through the use of vacuum. A partial vacuum placed over the clitoris creates negative pressure in the organ and promotes clitoral arterial inflow which, in turn, results in increased vascular engorgement and sexual arousal. Embodiments of a device for stimulating female sexual response that is designed to be applied in the clitoral region are described in U.S. Pat. No. 6,733,438 ("the '438 patent") entitled "Female Stimulation Device," which issued on May 11, 2004, and which is incorporated herein by reference in its entirety. The '438 patent describes embodiments of a device that is placed over the clitoris of the user and produces a vacuum to stimulate blood flow and sexual response. The '438 patent also mentions the use of a lubricant with the device to, for example, enhance the vacuum seal. The '438 patent also mentions that the lubricant can be disposed on a body-contacting surface of a flange included in the device.

There are application, manufacturing, automation and packaging difficulties in applying the biocompatible substance to the device. For example, the biocompatible substance can be difficult to apply in an automated fashion since the biocompatible substance can leak, desiccate, dry, migrate, or in the manufacturing process, can be expensive or technically difficult to apply. Maintaining the biocompatible substance within the device provides cost savings and convenience in that it does not require additional separate packaging.

SUMMARY OF INVENTION

Embodiments of the invention provide a simple, reliable, inexpensive device, system and method of applying a biocompatible substance to a female sexual stimulation device.

In one aspect, the invention provides a female stimulation system that includes a device body having an operating region and a body contacting surface, and means for controlling a vacuum produced by the device body when the device body is applied to a user. In addition, the female stimulation system includes means for applying a biocompatible substance to the body contacting surface. In one or more embodiments, the applicator may be a pad, form-fitted insert, or a capsule.

In another aspect, the invention provides a female stimulation system that includes a device body having an operating region comprising a vacuum producing chamber and a body contacting surface, and means for controlling vacuum produced by the device body when applied to a user. In addition, the system includes an applicator adapted to apply a biocompatible substance to the body contacting surface. The biocompatible substance is stored within a storage region on the applicator.

In another aspect, the invention provides a female stimulation device kit including a female stimulation device with a device body that includes an operating region comprising a vacuum producing chamber, a body contacting surface, and means for controlling a vacuum produced by the device when the device is applied to the user. In addition, the female stimulation device kit includes an applicator configured to apply a biocompatible substance to the body contacting surface.

In yet another aspect, the invention provides a method of facilitating female stimulation including an act of providing a female stimulation device including an operating region comprising a vacuum producing chamber, a body contacting surface, and means for controlling a vacuum produced by the device to promote clitoral blood flow. In addition, the method includes an act of providing means for applying a biocompatible substance to the body contacting surface.

In a further aspect, the invention provides a method for enhancing female stimulation including acts of providing a female stimulation device comprising an operating region which defines a vacuum chamber and a body contacting surface, providing means for applying a biocompatible substance to the body contacting surface, placing the device over the female clitoris such that the body contacting surface is placed into contact with vaginal tissue, compressing at least a portion of the operating region to discharge air from the vacuum chamber, and releasing the operating region to produce vacuum levels that promote clitoral blood flow.

In a further aspect, the invention provides an applicator for applying a biocompatible substance to a female stimulation device that includes a body contacting surface which is adapted to provide a seal about a female clitoris. The applicator includes a surface sized and shaped to store and to apply the biocompatible substance to the body contacting surface.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
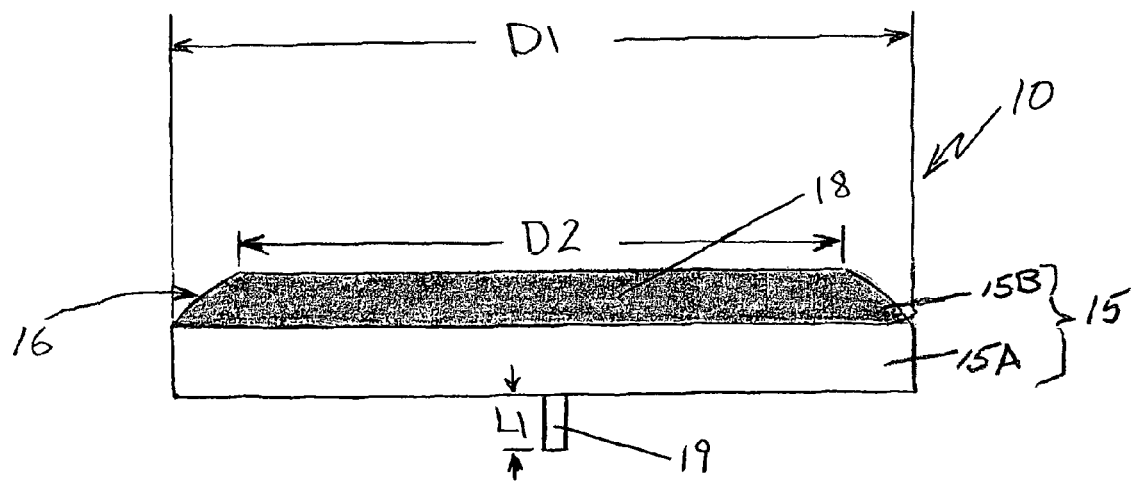
FIG. 1A is a cross sectional side view of an applicator including a biocompatible substance in accordance with one embodiment.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

In accordance with one or more embodiments, an applicator is provided for applying a biocompatible substance such as a lubricant, cream, liquid, lotion, hydrophilic material, gel or pharmacologically active material to a female sexual stimulation device. In various embodiments, the applicator includes a storage region that contains the biocompatible substance for use with the female sexual stimulation device. As used herein, the term "storage region" refers to any portion of the applicator that contains a biocompatible substance for use with the female sexual stimulation device. The applicator may be provided in the form of a pad, an insert, a capsule, a combination of two or more of the preceding, or a combination including any of the preceding and other structure. Where the applicator is a pad, for example, the storage region may be on a surface of the pad. Further, where the applicator is a capsule, the storage region can be located within an interior chamber defined by the walls of the capsule.

According to one embodiment, the applicator may include a pad of material constructed of any impermeable (for example, non-woven or pullulan film) material with a biocompatible substance layered on its surface, or a permeable (for example, woven) material with a biocompatible substance impregnated into its interstices. In some embodiments, the applicator 15 is separately packaged from the female sexual stimulation device while in other embodiments the applicator is packaged or otherwise supplied in a kit that includes the female sexual stimulation device. In use, the user may open the package, remove the applicator and coat a body contacting surface of the female stimulation device with the biocompatible substance using the applicator. In further embodiments, the applicator may either be positioned against the body contacting surface and/or inside an interior vacuum chamber of the device. In another embodiment, an applicator includes a pad with a handle which is sized and shaped to facilitate placement of the biocompatible substance on the female sexual stimulation device.

In further embodiments, the applicator is sized and shaped to fit within the interior vacuum chamber of the female sexual stimulation device and/or sized and shaped to engage the body contacting surface of the device. In these embodiments, the biocompatible substance may be placed on the surface of a rim of the applicator which, in turn, contacts the body contacting surface of the female sexual stimulation device. In yet another embodiment, the biocompatible substance may be stored within the applicator to be removed and applied by the user. The biocompatible substance applied to the pad may be any aqueous, petroleum or silicone based gel or pharmacologically active gel.

In another embodiment, the applicator consists of a deformtable, or partially deformable, storage capsule. The biocompatible material can be placed within the interior of the capsule, e.g., within a storage region. When the storage capsule is compressed, the wall of the storage capsule ruptures and the biocompatible substance is released from the cavity formed by walls of the capsule to be applied to the female sexual stimulation device. In another embodiment, the storage capsule is placed within the tip of the female sexual stimulation device and ruptures upon compression of the tip. The outer wall of the storage capsule may contain indentations or perforations to facilitate rupture of the wall or egress of the biocompatible substance, i.e., the storage region includes a releasable seal. In yet another embodiment, the storage capsule has a plurality of small perforations circumferentially surrounding the outer wall which facilitates the tearing of the capsule and release of the biocompatible substance. The capsule can be composed of any deformable material, preferably a gel capsule such as gelatin, water soluble polysaccharides (for example pullulan), or hydroxypropylmethylcellulose.

In accordance with one or more embodiments, a method for applying lubricant to a body contacting surface of a female sexual stimulation device is provided. In one embodiment, the method includes an applicator which consists of a pad with a biocompatible substance applied to its surface (for example, layered) or impregnated into its interstices. The pad may be packaged separately or included with the female sexual stimulation device. In use, the user can remove the pad and apply the biocompatible substance to the rim of the female sexual stimulation device. In another embodiment, the applicator consists of a deformable storage capsule containing the biocompatible substance. In use, the user compresses the storage capsule and releases the biocompatible substance for application to the female sexual stimulation device. In various embodiments, the storage capsule can be packaged separately or within the female sexual stimulation device. With these arrangements, a simple, controlled method to apply the biocompatible substance to a female stimulation device is described.

Figure 1B:
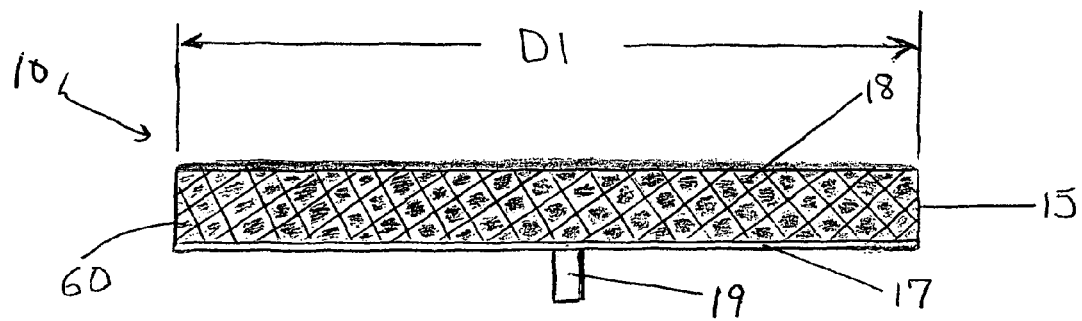
FIG. 1B is a cross sectional side view of another embodiment of an applicator including a biocompatible substance.

Referring to FIGS. 1A and 1B, an applicator 10 is described consisting of a pad of material 15 with a biocompatible substance 18 disposed proximate a surface 16 of the pad. For example, where the pad 15 is impermeable, the biocompatible substance may be disposed on the surface 16, for example, the surface is coated with the substance. Alternatively, where the pad 15 is permeable, the biocompatible substance may be disposed within interstices (for example, pores) included in the surface. Referring to FIG. 1A, the pad 15 may include an impermeable (for example non-woven pullulan film) material with the biocompatible substance 18 coated on the surface 16 of the pad. Referring to an alternative embodiment in FIG. 1B, the pad 15 may also include any permeable (for example woven) material with the lubricant 18 impregnated into interstices 60 of the pad 15. When the pad 15 is pressed against another surface, such as a body contacting surface of a female sexual stimulation device, biocompatible material will escape from the interstices and coat the surface of the device. In one embodiment where the pad 15 is permeable, the pad 15 may include a base 17 that includes a separate impermeable layer or coating of material which may be used to prevent leakage or migration of the lubricant. Embodiments that include a pad 15 that is impermeable may also include a base 17. A handle 19 may also be attached to the base 17 of the pad 15 to facilitate application of the lubricant 18 and manipulation of the lubricant applicator 10. In one embodiment, the handle has a length L1 which is sufficient to allow a user to apply the biocompatible substance in the correct amount without waste. The shape of the pad 15 may vary, for example, the shape may be circular, square, or spherical. In addition, in one or more embodiments the pad 15 is sized and shaped to fit within, or be appended to, a female sexual stimulation device, for example, within an interior vacuum chamber of the female sexual stimulation device. The biocompatible substance can be any aqueous, petroleum or silicone based lubricant, cream, liquid, lotion, hydrophilic material, gel, or consist of a pharmacologically active material, any combination of the preceding substances or any combination of the preceding substances and one or more additional biocompatible substances. In one embodiment, the biocompatible substance may be an aqueous based lubricant. In further embodiments, the biocompatible substance may be heated, have a fragrant scent or pleasant taste so as to further enhance the effect.

According to one embodiment, the pad 15 includes a first diameter D1 which may, for example, be a maximum width of the pad 15. In a-version of this embodiment, the pad has a circular shape and the first diameter D1 is a constant diameter. As mentioned above, the pad 15 may be in a shape other than circular, for example, the pad may be a square shape, an oval shape, or an elliptical shape. Further, in one embodiment, the pad may include a first region 15A with the first diameter D1 and a second region 15B that is graduated from the first diameter D1 to a second diameter D2. In the embodiment illustrated in FIG. 1A, the second diameter D2 is smaller than the first diameter D1 and the surface 16 has a substantially uniform decrease in diameter from the diameter D1 to the diameter D2 (for example, the surface has a constant slope).

Figure 2A:
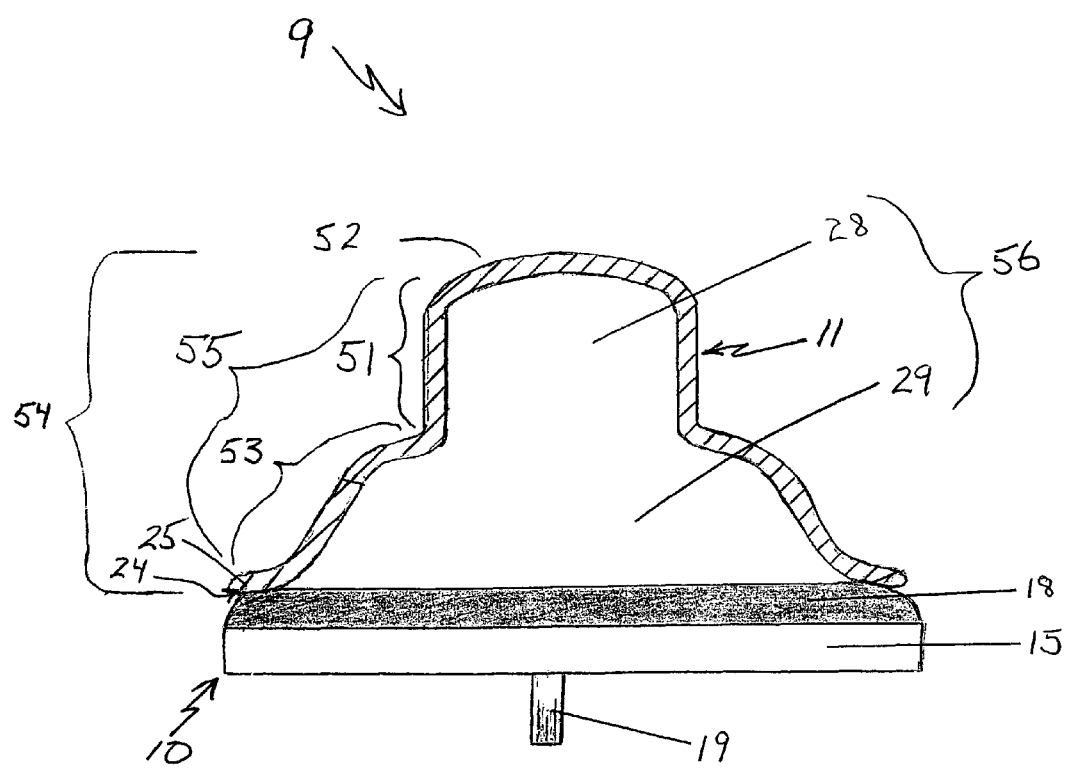
FIG. 2A is a cross sectional side view of an embodiment of an applicator and a female stimulation device where the applicator contacts a body contacting surface of the female stimulation device.

As mentioned above, embodiments of the applicators 10 are employed with a female sexual stimulation device. FIG. 2A illustrates an embodiment of a female stimulation system 9 that according to one embodiment includes the applicator 10 and a female stimulation device 11. The female stimulation device 11 includes a device body 54 including an operating region 55 and a body contacting surface 24. In addition, the device body 54 may define an interior region 56. In one embodiment, the interior region 56 includes an upper vacuum chamber 28 and a lower vacuum chamber 29. The device 11 may also include an end wall 52. The operating region may be employed by a user to manipulate the female stimulation device 11. For example, the user may grip the device body by a first portion 51 (for example, a tip portion) and/or a second portion 53 (for example, an intermediate side wall portion) to place the device over the female clitoris. In addition, the user may apply pressure to one or more regions of the operating region (for example, the user may apply pressure to the first portion) to create a vacuum within one or more of the vacuum chambers 28, 29.

According to one embodiment, the device body 54 may also include a flange 25 where the flange 25 includes the body contacting surface 24. The device body 54 need not include the flange 25, however, provided that a body contacting surface is included in the female stimulation device 11. The body contacting surface 24 is positioned to provide a seal around the female clitoris when the female stimulation device 11 is employed by the user. As noted above, and according to another embodiment, the device body 54 may also include an intermediate side wall portion that may be substantially non-deformable in response to deformation of a tip portion. The tip portion may be deformable while the intermediate side wall portion may retain its shape, serving as a vacuum reservoir and/or a lower chamber.

The female stimulation device 11 may include a wide variety of shapes in addition to the shape illustrated in FIG. 2A. For example, the device body may be formed in any shape provided that the female stimulation device 11 includes both a body contacting surface and an operating region that provides the user with the ability to control the amount of vacuum drawn by the device.

In accordance with one embodiment, the female stimulation system 9 may include both a female stimulation device and an applicator. In such a system, the applicator may be any device sized and shaped to apply a biocompatible substance to a body contacting surface of the female stimulation device. In another embodiment, the female stimulation system 9 may include only a female stimulation device where, for example, a storage capsule is located proximate the body contacting surface or another surface of the stimulation device.

Figure 2B:
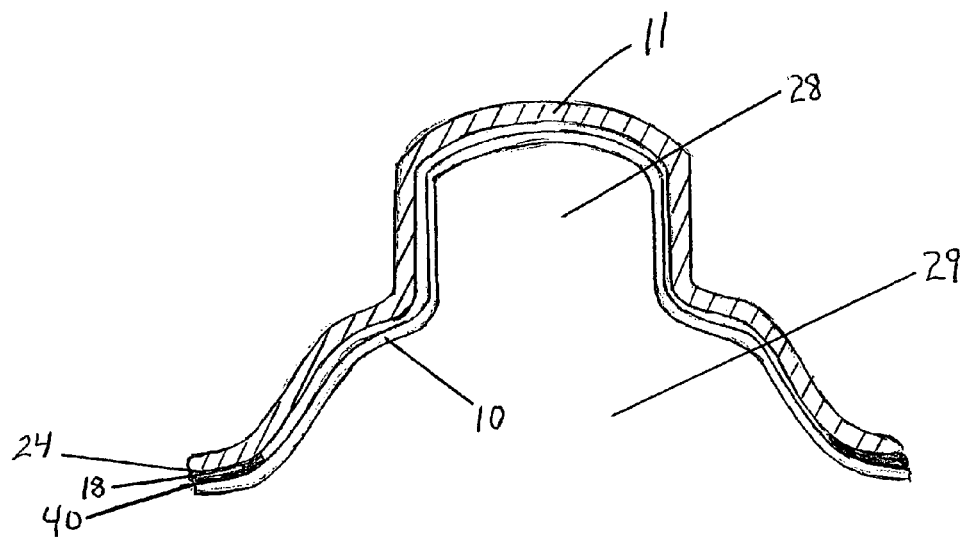
FIG. 2B is a cross sectional side view of an applicator sized and shaped to fit within an interior of a female stimulation device in accordance with one embodiment.

The applicator 10 can be packaged separately from the female sexual stimulation device. Alternatively, the applicator 10 can be packaged with the female sexual stimulation device, for example, in a kit. Referring to FIG. 2A, the applicator 10 may also be packaged so that the lubricant 18 is in contact with the body contacting surface 24 of the female sexual stimulation device 11. Referring to FIG. 2B, in one embodiment, the applicator 10 can be sized and shaped to fit within an interior vacuum chamber of the female sexual stimulation device, for example, within either or both of the upper vacuum chamber 28 and the lower vacuum chamber 29 as an insert. In a version of this embodiment, the biocompatible material 18 is disposed on a storage region 40 of the applicator 10. In embodiments where the applicator 10 is packaged with female stimulation device 11, the user can open the package containing both the applicator 10 and the female sexual stimulation device 11 and simply remove the applicator 10 which has already been in contact with the body contacting surface 24. As a result, the body contacting surface 24 is prelubricated in the package, and the device 11 is ready for use when the applicator 10 (for example, insert) is removed.

Figure 2C:
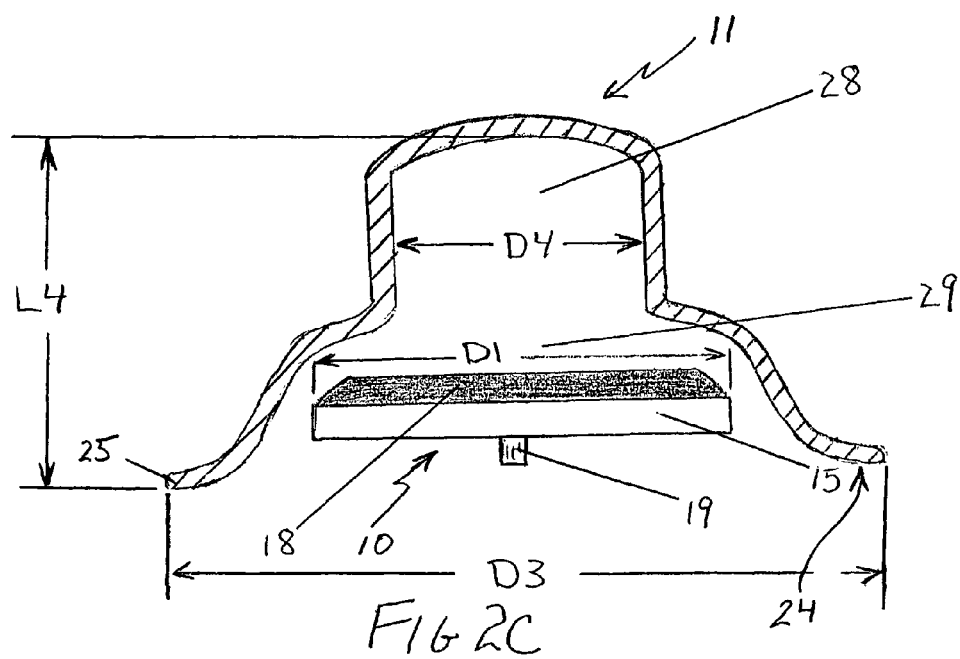
FIG. 2C is a cross sectional side view of an applicator and a female stimulation device where the applicator is sized and shaped to fit within the interior of the female stimulation device in accordance with another embodiment.

Referring to FIG. 2C, the applicator 10 can be placed within an interior vacuum chamber of the female sexual stimulation device for storage (for example, within either or both of the upper vacuum chamber 28 and the lower vacuum chamber 29). In one embodiment, the user can open the package containing both the applicator 10 and the female sexual stimulation device 11, remove the applicator 10 from the inside of the device 11, apply the biocompatible substance 18 to the body contacting surface 24 and discard the applicator 10. According to one embodiment, the first region 51 has a diameter D4 that defines the upper vacuum chamber 28 and the flange 25 has a diameter D3. In one embodiment, the diameter D1 of the applicator 10 is less than the diameter D3 and greater than the diameter D4. As a result, the applicator 10 can be stored within the portion of the device body 54 that defines the lower vacuum chamber 29. In one embodiment, the dimension D3 may vary between about 0.50 cm and about 1.75 cm. Further, the dimension D4 may vary in proportion to the dimensions stated above, but generally will be between about 0.25 cm and about 0.75 cm.

Figure 2D:
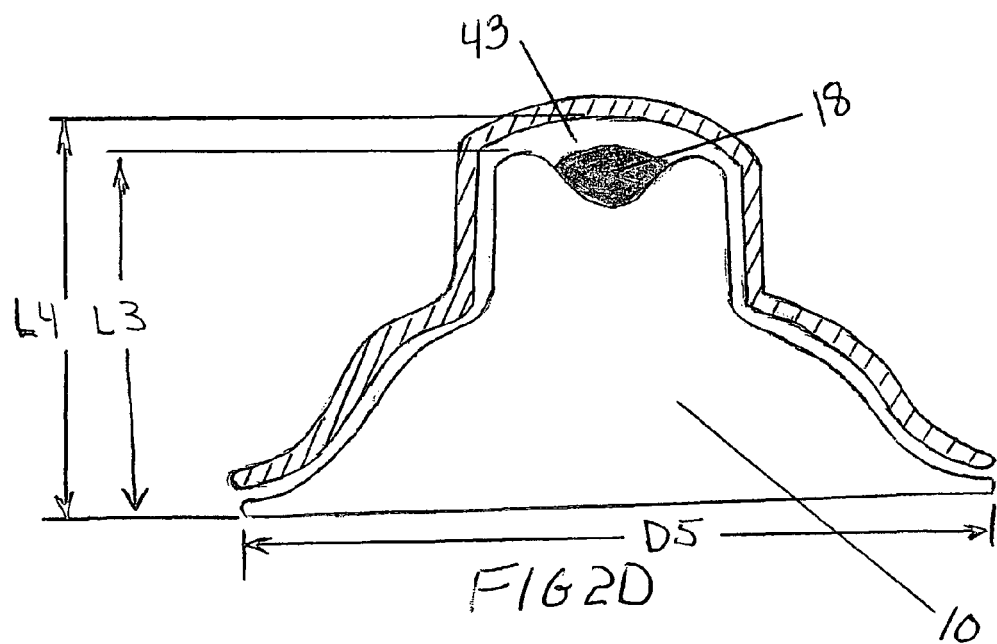
FIG. 2D is a cross sectional side view of a yet another embodiment of an applicator and a female stimulation device where the applicator is sized and shaped to fit within an interior of the female stimulation device.

In yet another embodiment, referring to FIG. 2D, the applicator 10 can be sized and shaped to fit within a vacuum chamber (for example, chambers 28, 29) of the female sexual stimulation device 11 with the lubricant 18 stored within an interior of storage region 43 of the applicator 10. According to one embodiment, a pocket or recess defines the storage region. According to one embodiment, the user can open the package, remove the applicator, and apply the biocompatible substance to the female sexual stimulation device 11. In one embodiment, the applicator 10 is sized and shaped with a diameter D5 and a height L3. In a version of this embodiment, the applicator form-fits within the interior 56 of the device body 54. For example, in one version, the height L3 is substantially equal to a depth L4 of the device 11, and the diameter D5 is substantially equal to the diameter D3.

Figure 3:
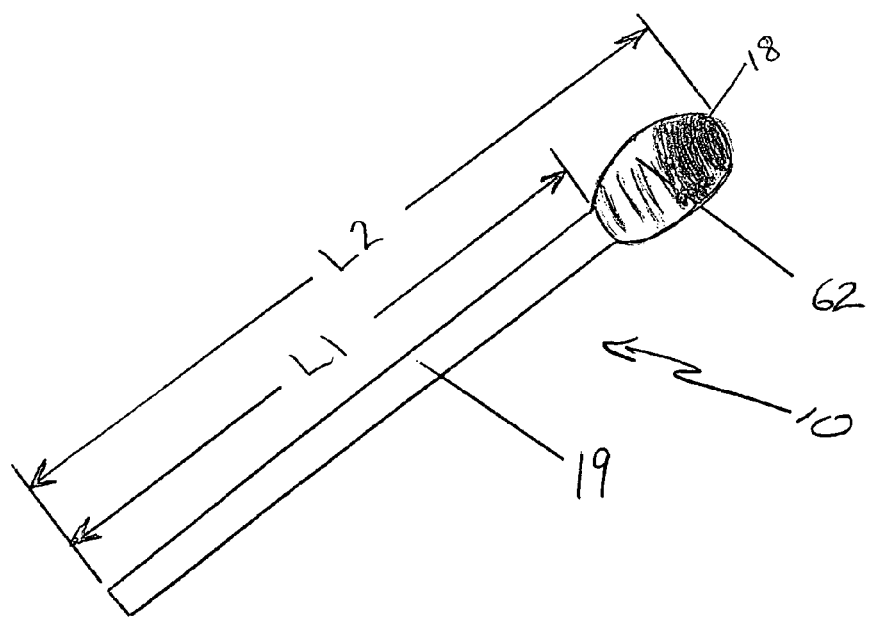
FIG. 3 is a side view of a further embodiment of an applicator sized and shaped for use with a female stimulation device.

Referring to FIG. 3, the applicator 10 may include a pad 62 of material with the biocompatible substance 18 applied to a surface of the pad 62. According to one embodiment, the pad 62 may be attached at a distal end of a handle 19. In one embodiment, the applicator 10 is sized and shaped to allow the user to place the biocompatible substance on one or more surfaces of the device 11. For example, either or both of an overall length L2 of the applicator or a length L1 of the handle 19 may be sized and shaped to allow the user to easily reach surfaces for lubrication. In a version of this embodiment, the user can utilize the handle 19 to manipulate the applicator 10 to apply biocompatible substance to the body contacting surface 24 of the female sexual stimulation device 11. The biocompatible substance may also be applied to other regions of the device 11, for example, the substance may be applied within the interior 56.

Figure 4:
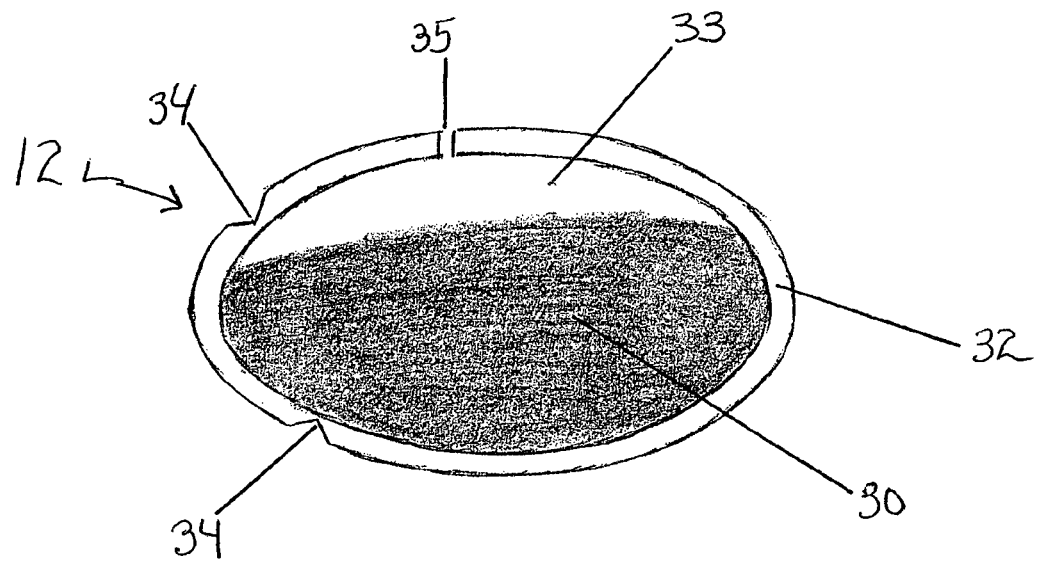
FIG. 4 is a cross sectional side view of a still further embodiment of an applicator sized and shaped for use with a female stimulation device.
Figure 5:
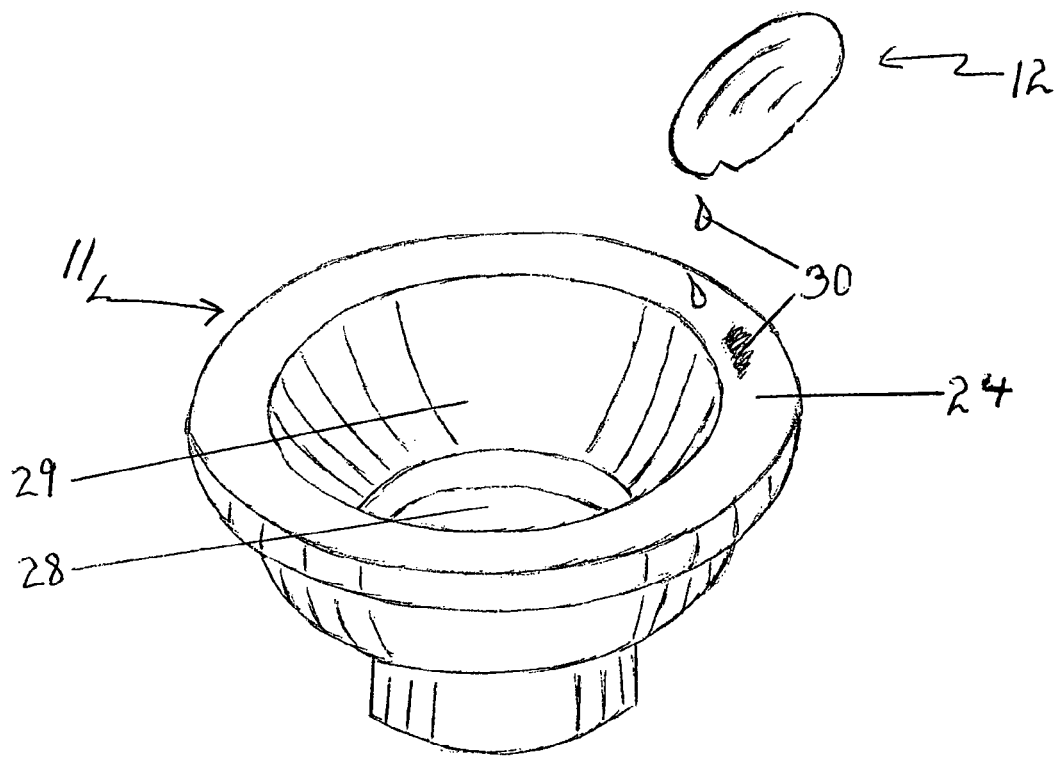
FIG. 5 is a perspective view of a biocompatible substance being applied to a female stimulation device with the applicator illustrated in FIG. 4 in accordance with one embodiment.
Figure 6:
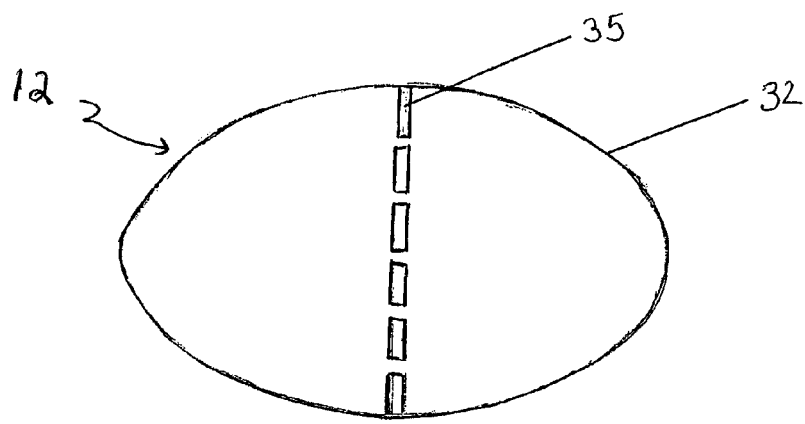
FIG. 6 illustrates an embodiment of the applicator of FIG. 4 where the applicator includes a plurality of perforations.

Referring to FIGS. 4 and 5, another embodiment of an applicator 12 is illustrated where the applicator can be a storage capsule with an outer wall 32 and a biocompatible substance 30 stored in a storage region 33 formed within its interior defined by the outer wall 32. To release the biocompatible substance 30, the user can compress the outer wall 32 of the applicator, thereby rupturing its wall. The biocompatible substance 30 may then be applied to the body contacting surface 24. To facilitate rupturing of the outer wall 32 and/or egress of the biocompatible substance 30, a single or a plurality of indentations 34, perforations 35 or a combination of each are created in the surface of the outer wall 32. The openings formed in the wall of the capsule are sized and shaped to allow a thin layer of biocompatible substance 30 to be applied to the body contacting surface of the device to avoid device slippage. In one embodiment, the openings formed in the wall of the capsule are sized and shaped to provide the controlled release of a predetermined amount of the biocompatible substance. In some embodiments, less than about 3 mm thickness of the biocompatible substance 30 may be applied to the body contacting surface of the device. In accordance with one embodiment, the perforations 35 circumferentially surround the outer wall 32, as illustrated in FIG. 6, to permit the user to easily tear the storage capsule, dispense the biocompatible substance from within the storage region 33 and apply the substance to the female sexual stimulation device.

The wall of the storage capsule 32 can be composed of any deformable (at least in part) material that ruptures upon compression. In one embodiment, the material may consist of (but is not limited to) a gel capsule such as gelatin, water soluble polysaccharides (for example, pullulan) or hydroxypropylmethylcellulose. The shape of the storage capsule can also vary, for example, it may be oblong, spherical or cylindrical. As previously described, the biocompatible substance can be any aqueous, petroleum or silicone based lubricant or a pharmacologically active gel.

Figure 7A:
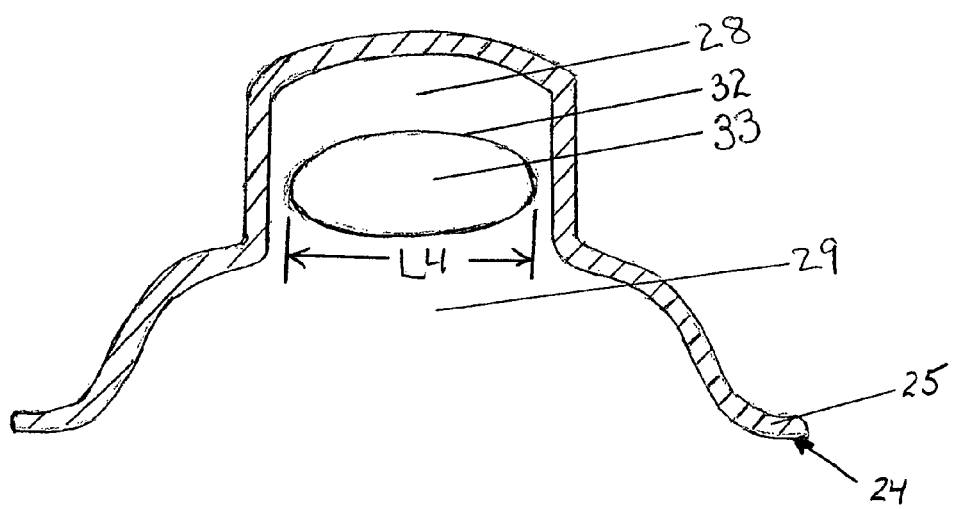
FIG. 7A is a cross sectional side view of an embodiment of the applicator of FIG. 4 where the applicator is sized and shaped to fit within a portion of a female stimulation device.

The applicator 12 can be packaged separately from the female sexual stimulation device 11. Alternatively, the storage capsule can be packaged with the female sexual stimulation device, for example, in a kit for treating female sexual dysfunction. Referring to FIG. 7A, in another embodiment, the storage capsule can be sized and shaped to be located within the first region 50 (for example, in the upper vacuum chamber 28) of the female sexual stimulation device 11. In a version of this embodiment, the outer wall of the storage capsule 32 is ruptured and lubricant 30 is released when the first region is compressed. The user may then remove the applicator and coat the body contacting surface 24 with the released biocompatible material. In one embodiment, a length L4 of the applicator 12 is sized to allow the applicator to fit within the chamber 28, i.e., length L4 is less than D4 as illustrated in FIG. 2C.

Figure 7B:
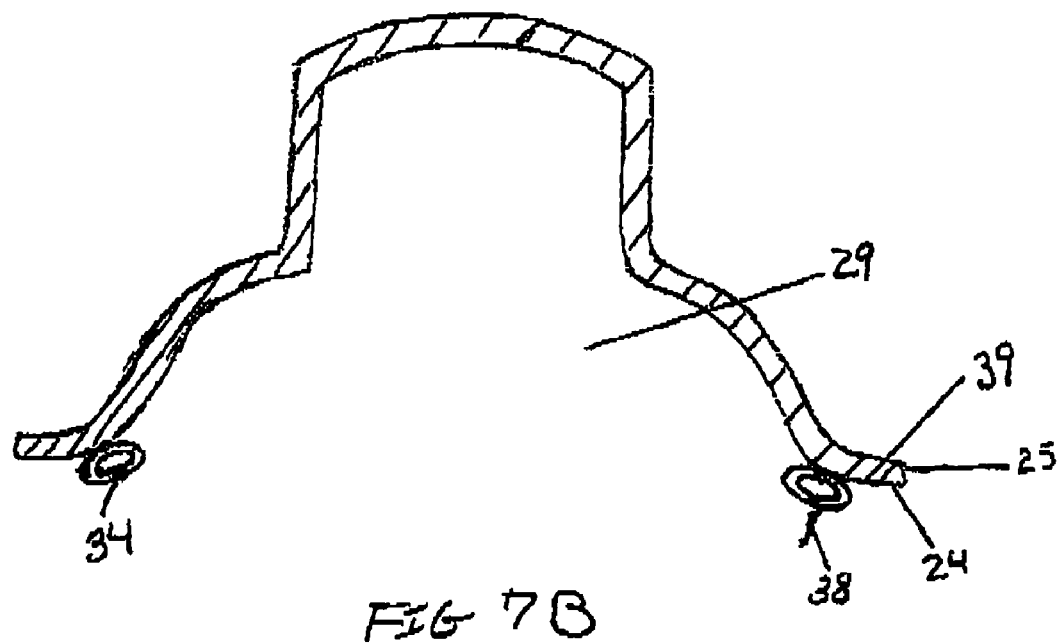
FIG. 7B is a cross sectional side view of an embodiment of the applicator located proximate to a body contacting surface of the female stimulation device in accordance with one embodiment.

Referring to FIG. 7B, an applicator in the form of a storage capsule 39 for storing a biocompatible substance can be sized and shaped to engage all or a portion of the body contacting surface 24. In one embodiment, the storage capsule 39 provides a sealed region where the biocompatible substance is stored proximate the body contacting surface 24 and the capsule 39 covers a portion of the body contacting surface 24. In one embodiment, the storage capsule 39 is donut-shaped. The storage capsule 39 may include a releasable seal. For example, the releasable seal can include perforations or indentations located in an outer wall of the storage capsule 39. In one version, the user compresses the storage capsule 39 to break the releasable seal and release the biocompatible substance onto the body contacting surface of the device. In yet another embodiment, a string 38 is imbedded into the wall of the storage capsule 39. The user pulls the free, nonimbedded end of the string 38 which tears the releasable seal 34 of the storage capsule 39 and releases the biocompatible substance. The end of the string may be adhered to an end of the storage capsule 39 so that the user pulls the releasable seal away from the body contacting surface 24 after the biocompatible substance has been applied. In any of the above embodiments, the storage capsule 39 may be fixed in place on the body contacting surface 24 during manufacture of the female sexual stimulation device.

Embodiments may provide a method of application of a biocompatible substance to a female sexual stimulation device with a pad 10, for example, as illustrated in FIGS. 1-3. In one embodiment, a piece of material 15 which has been impregnated or coated with a biocompatible substance 18 (e.g. lubricant, gel, cream, lotion, hydrophilic material or pharmacologically active material) is sealed in a package which may be included in a kit with a female sexual stimulation device. The user may open the package, remove the pre-lubricated pad 10 and place it in contact with the body contacting surface 24 of the female sexual stimulation device 11. When the biocompatible substance is applied to the body contacting surface 24, the applicator may be disposed of and the female sexual stimulation device may be applied to the clitoris. In another embodiment, a pre-lubricated pad 10 is packaged with the female sexual stimulation device. In several embodiments, the pad 10 is positioned to be in contact with the body contacting surface 24. The user merely opens the package and removes the applicator which is already in contact with the rim of the device. In another embodiment, a pre-lubricated pad 10 is stored within the interior vacuum chamber of the female sexual stimulation device or within the interior of the applicator 43. In a version of this embodiment, the user opens the package, removes the applicator from inside the stimulation device, applies the lubricant or other biocompatible substance 18 and discards the applicator. In another embodiment, the applicator has a handle 19 which allows the user to easily apply the lubricant to the female sexual stimulation device.

Embodiments may also provide a method of application of a lubricant to a female stimulation device using a deformable capsule 12 containing a lubricant or pharmacologically active gel 30. The user may rupture the capsule by compressing its outer sidewalls 32, thereby releasing the lubricant 30. The lubricant 30 may then be applied to the surface of the flange 25 of the female sexual stimulation device. As previously described, the applicator 12 may be a storage capsule which includes a single or plurality of indentations 34 or perforations 35 on its outer wall 32 to facilitate rupturing of the wall, egress of the lubricant or tearing of the capsule. In another embodiment, the applicator 12 is placed within the tip portion 28 of the female sexual stimulation device and is ruptured upon compression of the tip portion 28. In another embodiment, the storage capsule may be placed on the body contacting surface 24 of the female sexual stimulation device. For example, the storage capsule may be attached to the body contacting surface. A string may be imbedded in the outer wall to facilitate tearing of the storage capsule. The storage capsule can be constructed of any deformable material, preferably a gel capsule such as gelatin, water soluble polysaccharides (for example, pullulan), or hydroxypropylmethylcellulose.

Embodiments of the above described lubricant applicators are simple to manufacture, operate reliably, and may provide a measured amount of lubricant to the female sexual stimulation device. Furthermore, they prevent migration, desiccation and dissipation of the lubricant, thereby increasing the shelf life of the product.

In various embodiments, the biocompatible substance employed with the applicator may be any biocompatible lubricant. In one embodiment, the biocompatible material is selected from a group consisting of an adhesive, a lubricant, a vasoactive substance, and mixtures thereof. Further, the substance may include an adhesive material, a non-adhesive lubricant (for example, water-based gels, petroleum-based gels, or hydrophilic, water-soluble polymers, and the like), and/or pharmacologically active materials such as vasoactive agents. When applied in this manner, vasoactive agents may dilate blood vessels and increase clitoral blood flow. These materials include, but are not limited to: 1. vasoactive agents, both natural and synthetic, that act as vasodilators such as prostaglandins, endothelial-derived relaxation factors, vasoactive interstitial polypeptide agonists, smooth muscle relaxants, leukotriene inhibitors, L-arginine, and others; and 2. Medications and substances that increase clitoral stimulation such as estrogen, methyl testosterone, and apomorphine.

Any of the preceding embodiments may also be used in combination with any of additional structures and elements to increase or enhance clitoral blood flow and stimulation. For example, stimulation of the clitoris by suction can be aided by mechanical manipulation, vibratory motion, and/or heat. Therefore, the device for stimulating the clitoris of a female may further include additional structures and elements to increase or enhance clitoral blood flow and stimulation. Such structures may include mechanical attachments secured to the device to contact the clitoral tissue without compressing, obstructing or pinching. Another embodiment may include vibratory devices secured to a portion of device body, and electronically or mechanically operated to enhance clitoral blood flow. Another embodiment may include the use of a heat-producing compound on or in a surface-contacting portion of the device to stimulate the user. All of these supplemental structures may be used in combination with the vacuum producing device to increase the overall efficiency of the device and enhance stimulation of the user.

As noted, in addition to the vacuum portion, the device may also include mechanical attachments, such as a plurality of thin, flexible, soft attachments, secured to an interior aspect of the intermediate side wall or tip portion and dangling into the lower vacuum chamber housing the clitoris (after the device is applied by the user). After the device is applied, movement by the user would cause motion of these attachments, thereby creating additional clitoral stimulation by mechanical manipulation. In an alternative embodiment, the device may include a plurality of roller elements, which may have a spherical shape, contained within a channel placed around the device. Movement by the user would cause the elements to collide, thereby creating additional clitoral stimulation by vibratory effects. In yet another alternative embodiment, the device may include a vibrator motor. Before or after the device is applied by the user, the motor can be engaged, thereby creating additional clitoral stimulation by vibratory effects.

According to a further aspect of the invention, the inside of the device may be heated to provide increased warmth and vasodilation to the genital area. This heated effect can be accomplished by directly heating the device before application or by applying heat-generating compounds onto the flange or within the interior chamber of the device. The combination of heat and vacuum synergistically increase blood flow to the clitoris.

A method for increasing female sexual stimulation includes placing on the clitoris of the user a device body having a tip portion, a flange and an outwardly convex, intermediate side wall so that the device body encompasses the clitoris. Deforming the tip portion will create a vacuum within the interior chamber, thereby stimulating vascular engorgement and sexual arousal. The method further includes additional clitoral stimulation by at least one of mechanical manipulation by a plurality of mechanical attachments extending into the lower vacuum chamber; vibratory motion produced mechanically or electronically; or heating of tissue by compounds applied to the flange or inner surface of the interior chamber of the device.

With the arrangement of the device of the present invention, a small, simple, and effective female clitoral stimulation device provides suction and enhanced stimulation to the clitoris, thereby stimulating vascular engorgement and sexual arousal. Advantageously, the device does not require an external vacuum source or associated tubing or connections. The device is simple to use, permitting the user to perform her daily activities while wearing it in an undetectable and discreet fashion.

As noted above, the user can alter the amount of vacuum in the interior vacuum chamber by varying the degree of compression of the tip portion and thus the amount of air that is displaced. The greater the amount of manual compression to the tip portion, the greater the amount of displaced air and subsequent vacuum. In this manner, the user can advantageously regulate the amount of clitoral suction in order to generate a physiological response, rather than rely upon predetermined vacuum from an external vacuum source. The amount of vacuum necessary to stimulate female sexual arousal may vary depending upon the user and her pre-excitatory state but is preferable between about 40 mmHg and about 190 mmHg. Clinical testing has demonstrated that this negative pressure range maximizes clitoral blood flow without causing discomfort, bleeding and tissue injury.

Each of the various embodiments may include an applicator sized and shaped to provide the controlled release of a predetermined amount of the biocompatible substance. For example, where the applicator is any of a pad, an insert or a capsule the applicator may store a quantity of the biocompatible substance and be sized and shaped to apply less than about 3 mm thickness of the biocompatible substance to the body contacting surface of the device. The preceding approach may prevent over lubrication of the female sexual stimulation device.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A kit for female stimulation comprising a device body including a first portion defining an upper vacuum chamber having a first diameter, a second portion defining a lower vacuum chamber having a second diameter greater than the first diameter and a body contacting portion, having a third diameter greater than the second diameter wherein the second portion is connected between the first portion and the body contacting portion and an applicator having a diameter smaller than the third diameter and greater than the first diameter wherein the applicator includes a material to be applied to the inner surface of the second portion and is discarded before the device body is applied to the portion of the body to be stimulated.

2. The female stimulation system of claim 1, wherein said vacuum producing chamber produces vacuum levels of between about 40 and about 190 mmHg.

3. The female stimulation system of claim 1, further comprising a storage region comprising said biocompatible substance.

4. The female stimulation system of claim 3, wherein said applicator is a removable applicator.

5. The female stimulation system of claim 4, wherein said storage region is included on a surface of said removable applicator.

6. The female stimulation system of claim 5, wherein said storage region of said removable applicator engages said body contacting surface.

7. The female stimulation system of claim 4, wherein said device body defines a vacuum producing chamber, and said removable applicator is sized and shaped to fit within said vacuum producing chamber.

8. The female stimulation system of claim 7, wherein said storage region is located in said vacuum producing chamber.

9. The female stimulation system of claim 4, wherein said storage region includes a sealed region.

10. The female stimulation system of claim 9, wherein said applicator comprises a capsule.

11. The female stimulation system of claim 10, wherein said biocompatible substance is stored in said capsule.

12. The female stimulation system of claim 9, wherein said applicator includes a releasable seal comprising a plurality of perforations and/or indentations.

13. The female stimulation system of claim 4, wherein said applicator is a pad.

14. The female stimulation system of claim 13, wherein said pad includes permeable material.

15. The female stimulation system of claim 14, wherein said permeable material includes interstices.

16. The female stimulation system of claim 15, wherein said applicator further includes an impermeable material located on at least one side of said pad.

17. The female stimulation system of claim 4, wherein said applicator further includes a handle.

18. The female stimulation system of claim 3, wherein said storage region is located proximate said body contacting surface.

19. The female stimulation system of claim 18, wherein said applicator comprises a capsule.

20. The female stimulation system of claim 19, wherein said capsule includes a releasable seal.

21. The female stimulation system of claim 1, wherein said device body defines at least one vacuum chamber, and wherein said means for applying said biocompatible substance is sized and shaped to fit within said vacuum chamber.

22. The female stimulation system of claim 1, wherein said body contacting surface is sized and shaped to encompass a female clitoris.

23. The female stimulation system of claim 1, wherein the biocompatible substance is a material selected from a group consisting of an adhesive, a lubricant, a lotion, a gel, a cream, a hydrophilic material, a pharmacologically active substance, and mixtures thereof.

24. A kit for female stimulation comprising a device body including a first portion defining an upper vacuum chamber having a first diameter, a second portion defining a lower vacuum chamber having a second diameter greater than the first diameter and a body contacting portion, having a third diameter greater than the second diameter wherein the second portion is connected between the first portion and the body contacting portion and an applicator form fitting and filling substantially the entire device body wherein the applicator includes a material to be applied to the inner surface of the device body and the applicator is discarded before the device body is applied to the portion of the body to be stimulated.

25. The female stimulation device kit of claim 24, wherein at least a first portion of said operating region is deformable, and wherein said vacuum is produced by deforming said at least first portion.

26. The female stimulation device kit of claim 24, further comprising instructions to apply said biocompatible substance to said device, and said device to said user.

27. The female stimulation device kit of claim 24, further comprising the biocompatible substance.

28. The female stimulation device kit of claim 27, wherein the biocompatible substance is a material selected from a group consisting of an adhesive, a lubricant, a vasoactive substance, and mixtures thereof.

29. The female stimulation device kit of claim 24, wherein said applicator includes a sealed region, and said biocompatible substance is included in said sealed region.

30. The female stimulation device kit of claim 24, wherein said applicator includes a pad.

31. The female stimulation device kit of claim 30, wherein the pad includes a storage region and the biocompatible substance is stored in the storage region.

32. The female stimulation device kit of claim 31, wherein the storage region is located on a surface of the pad.

33. The female stimulation device kit of claim 31, wherein the storage region is located in interstices included in a surface of the pad.

34. The female stimulation device kit of claim 24, wherein the applicator is included as a part of the female stimulation device.

35. The female stimulation device kit of claim 24, wherein said applicator is sized and shaped to fit within said device body.

36. A kit for female stimulation comprising a device body including a first portion defining an upper vacuum chamber having a first diameter, a second portion defining a lower vacuum chamber having a second diameter greater than the first diameter and a body contacting portion, having a third diameter greater than the second diameter wherein the second portion is connected between the first portion and the body contacting portion and a soluble capsule applicator fitted in the upper vacuum chamber wherein the applicator includes a material to be applied to the inner surface of the device body and ruptures upon compression of the device body.

37. A method for facilitating female stimulation, comprising acts of: providing a female stimulation device including an operating region comprising a vacuum producing chamber, a body contacting surface, and means for controlling a vacuum produced by
said device to promote clitoral blood flow; and providing means for applying a biocompatible substance to said body contacting surface, wherein the means for applying a biocompatible substance includes a storage region where the biocompatible substance is stored; and further comprising an act of breaking a seal to access said biocompatible substance and of placing said storage region in contact with said body contacting surface.

38. The method of claim 37, further comprising an act of providing instruction to apply said device.

39. The method of claim 37, further comprising an act of releasing said biocompatible substance from said storage region.

40. The method of claim 37, wherein said means for controlling the vacuum produce vacuum levels between about 40 and 190 mmHg.

41. The method of claim 40, wherein said means for applying said biocompatible substance is at least partially located within a vacuum chamber formed by the female stimulation device.

42. The method of claim 37, further comprising an act of releasing the biocompatible substance from the storage region when the means for controlling the vacuum is operated.

43. The method of claim 37, wherein the means for applying a biocompatible substance comprises a pad.

44. The method of claim 37, wherein the means for applying a biocompatible substance comprises a capsule.

45. The method of claim 37, wherein the means for applying a biocompatible substance comprises an applicator sized and shaped to fit within the female stimulation device.

46. A method for enhancing female stimulation, comprising acts of: providing a female stimulation device comprising an operating region which defines a vacuum chamber, and a body contacting surface; providing means for applying a biocompatible substance to said body contacting surface; placing said device over said female clitoris such that said body contacting surface is placed into contact with vaginal vault tissue; compressing at least a portion of said operating region to discharge air from said vacuum chamber; and releasing said operating region to produce vacuum levels that promote clitoral blood flow, further comprising an act of removing said device after a predetermined period of time.

47. The method of claim 46, wherein said vacuum levels are between about 40 and about 190 mmHg within said vacuum chamber.

48. The method of claim 46, wherein said means for controlling vacuum comprises at least one projection disposed within said operating region.

49. The method of claim 46, wherein said means for applying said biocompatible substance includes an applicator having a storage region where said biocompatible substance is stored.

50. The method of claim 49, further comprising placing said storage region in contact with said body contacting surface.

51. The method of claim 49, wherein the means for applying said biocompatible substance comprises a pad.

52. The method of claim 49, wherein the means for applying said biocompatible substance comprises a capsule.

53. The method of claim 52, wherein said capsule is located annularly about said body contacting surface.

54. The method of claim 49, wherein the means for applying said biocompatible substance comprises an applicator sized and shaped to fit within the female stimulation device.

55. The method of claim 46, wherein the method further comprises an act of releasing said biocompatible substance from a sealed region.

56. The method of claim 46, wherein said female stimulation device includes said means for applying said biocompatible substance.

* * * * *